US006765101B1

(12) United States Patent
Bhasin et al.

(10) Patent No.: US 6,765,101 B1
(45) Date of Patent: Jul. 20, 2004

(54) SYNTHESIS OF LOWER ALKYLENE OXIDES AND LOWER ALKYLENE GLYCOLS FROM LOWER ALKANES AND/OR LOWER ALKENES

(75) Inventors: Madan Mohan Bhasin, Charleston, WV (US); Stephen Wayne King, Scott Depot, WV (US)

(73) Assignee: Union Carbide Chemicals & Plastics Technology Corporation, Danbury, CT (US)

(*) Notice: Subject to any disclaimer, the term of this patent is extended or adjusted under 35 U.S.C. 154(b) by 21 days.

(21) Appl. No.: 09/846,642

(22) Filed: May 1, 2001

(51) Int. Cl.[7] ...................... C07D 301/03; C07D 303/00
(52) U.S. Cl. ...................................... 549/523; 549/513
(58) Field of Search ................................ 549/523, 513

(56) References Cited

U.S. PATENT DOCUMENTS

| | | | |
|---|---|---|---|
| 2,125,333 A | 8/1938 | Carter | 260/54 |
| 2,178,454 A | 10/1939 | Metzger et al. | 260/348 |
| 2,238,474 A | 4/1941 | McNamee et al. | 260/348 |
| 2,437,930 A | 3/1948 | Bergsteinsson et al. | 260/348.5 |
| 3,350,422 A | 10/1967 | Kollar | 260/348.5 |
| 3,987,069 A | 10/1976 | Barone | 260/348.5 |
| 4,130,570 A | 12/1978 | Boreskov et al. | 260/348.35 |
| 4,390,739 A | 6/1983 | Michaelson et al. | 568/860 |
| 4,413,151 A | 11/1983 | Michaelson et al. | 568/860 |
| 4,496,778 A | 1/1985 | Myers et al. | 568/860 |
| 4,508,927 A * | 4/1985 | Bhise et al. | |
| 4,990,632 A | 2/1991 | Ramachandran et al. | 549/523 |
| 5,008,412 A | 4/1991 | Ramachandran et al. | 549/523 |
| 5,008,414 A | 4/1991 | Ramachandran et al. | 549/538 |
| 5,043,461 A | 8/1991 | Ramachandran et al. | 549/523 |
| 5,344,946 A | 9/1994 | Warwel et al. | 549/531 |
| 5,929,258 A | 7/1999 | Hayashi et al. | 549/523 |
| 6,156,938 A | 12/2000 | Sobolev et al. | 568/800 |

FOREIGN PATENT DOCUMENTS

| | | | |
|---|---|---|---|
| EP | 0 077 202 | 4/1983 | ........... C07C/29/03 |
| EP | 484136 | 1/1996 | |
| GB | 2 129 800 A | 5/1984 | ........... C07C/29/48 |
| WO | WO 98/19983 | 5/1998 | ........... C07C/29/48 |

OTHER PUBLICATIONS

Bukhtiyarov, V. I. et al., "XPS Study of the size effect in Ethane Epoxidation on Supported Silver Catalysts," *Journal of Chem. Society*, vol. 39, No. 13, 1997, pp. 2323–2329. XP002213249.
Sen, A. et al., *Journal of American Chemical Society*, vol. 116, No. 3, 1994 pp. 998–1003. XP002213250.
Talsi, E. P. et al., *Journal of Chem. Soc. Chem. Communications*, No. 24, 1985, pp. 1768–1769. XP002213251.

McBee et al., *Ind. Eng. Chem.*, vol. 37, 1945, p. 434. XP002213252.
Soeylemez, T., et al., *Journal of Chem. Soc.* Perkins Trans 2, 1980, pp. 391–394. XP002213253.
Wan et al., *Ind. Eng. Chem.* vol. 45, 1953, p. 234. XP002213254.
Rastaturin, V. A.., *Journal of Appl. Chem.* vol. 57, No. 6, 1984, pp. 1225–1229. XP002213255.
Retamoso, R. M., et al., *Journal of Phys. Chem.* vol. 63, No. 5, 1989, pp. 707–709. XP002213256.
Journal of American Chemical Society; "A New Reaction. Stereospecific Vicinal Oxyamination of Ofefins by Alkyl Imido Osmium Compounds" Apr. 16, 1975.
J. Org. Chem., vol. 41, No. 1; Osmium–Catalyzed Vicinal Oxyamination of Olefins by Chloramine–T; 1975.
Journal of Catalysts; "Selective Catalytic Oxidation of Acetonitrile" 1986.
Angew. Chem. Int. Ed. Engl.; "Catalytic Asymmetric Aminohydroxylation (AA) of Olefins" 1996. 35 No. 4.
Catalysis Today; "Size–and support–dependency in the catalysis of gold" by Haruta 1997.
Jouranl of Catalysis; "Partial Oxidation of Ethane by Reductively Activated Oxygen over Iron Phosphate Catalyst" 1997.
Catalysis Today; "Generation of active oxygen species on solid surfaces." By Panov et al. 1998.
Journal of Catalysis; "Ammoxidation of Ethane to Acetonitrile over Metal–Zeolite Catalysts" by Lee et al. 1998.
Angew. Chem. Int. Ed. "Atom–Efficient Oxidation of Alkenes with Molecular Oxygen:Synthesis of Diols" Dobler et al. 1999.
Boreskov Insititue of Catalysis; "Advances in Oxidation Catalysis" 1999.
Angew. Chem. Int. Ed. Engl.; "Designing a Molecular Sieve Catalyst for the Aerial Oxidation of n–Hexane to Adipic Acid" 2000.

* cited by examiner

Primary Examiner—Alan L. Rotman
Assistant Examiner—Raymond Covington
(74) Attorney, Agent, or Firm—Tai-Sam Choo; Edward W. Rilee

(57) ABSTRACT

A method and apparatus for synthesizing at least one of alkylene oxides and alkylene glycols from lower alkanes and/or lower alkenes. In the preferred embodiment, the apparatus includes a lower alkane/alkene supply; an oxygen supply for providing a source of oxygen; and a metal oxide catalytic reactor. The metal oxide catalytic reactor includes a reactor chamber; and a catalyst in the chamber for reacting the lower alkane/alkene supply with the source of oxygen to convert the lower alkane/alkene by selective partial oxidation to at least one of the alkylene oxides and alkylene glycols. Also, in the preferred embodiment, a separator, downstream from the reactor, separates the alkylene oxides and alkylene glycols from the total product stream and the unconverted reactants.

15 Claims, 5 Drawing Sheets

SYNTHESIS OF LOWER ALKYLENE OXIDES AND LOWER ALKYLENE GLYCOLS FROM LOWER ALKANES AND/OR LOWER ALKENES

BACKGROUND OF THE INVENTION (1) Field of the Invention

The present invention relates generally to the synthesis of lower alkylene oxides and lower alkylene glycols and, more particularly, to a method and apparatus for the synthesis of lower alkylene oxides and lower alkylene glycols from lower alkanes and/or alkenes by selective partial oxidation.

(2) Description of the Prior Art

Ethylene oxide (EO) and ethylene glycol are currently manufactured from ethane and/or ethylene through a capital intensive, multi-step process. This conventional process utilizes a thermal cracker to make ethylene and other olefin hydrocarbons from ethane, propane, butane or naphtha hydrocarbons. The ethylene is separated from other byproducts, and is then epoxidized over a silver catalyst to produce ethylene oxide and other products including water and carbon dioxide. The ethylene oxide is then separated from these other reaction products and unconverted reactants. For further conversion to ethylene glycol (1,2-ethanediol or MEG), the ethylene oxide is mixed with a ten-fold or greater ratio of water and thermally hydrolyzed, though selective catalytic routes for EO to MEG are also currently being investigated.

Propylene glycol (1,2 propanediol or MPG) is similarly produced by hydrolysis of propylene oxide. The production of propylene oxide from propylene first requires production of a chlorohydrin intermediate by reacting propylene with chlorine and water. The chlorohydrin intermediate is then reacted with sodium hydroxide or calcium hydroxide to produce propylene oxide and sodium chloride or calcium chloride. A large volume of chloride salt byproducts is produced, and disposal of these salts is costly.

Other indirect routes are also known for producing propylene oxide. For example, isobutane can be reacted with oxygen to form t-butyl hydroperoxide, which in turn is reacted with propylene to produce propylene oxide and tert-butanol. The tert-butanol can then be reacted with methanol to produce the co-product methyl tertiary butyl ether (MTBE), a common gasoline additive. In another process, ethyl benzene is used as a starting material, and styrene is a resultant co-product. In each of these known processes for production of propylene oxide, a co-product results. Even though these co-products may sometimes be beneficial, they must always be handled and disposed of, and add accordingly to the cost of propylene oxide production.

Therefore, a process which could produce ethylene oxide, ethylene glycol, propylene oxide, propylene glycol, and other lower alkylene oxides and lower alkylene glycols directly from lower alkanes and/or lower alkenes as the starting hydrocarbon raw materials would provide a desirable advantage over the current prior art. For example, capital costs may be reduced by as much as fifty percent by eliminating the need for thermal crackers and associated equipment. A simpler manufacturing process would also reduce production costs and cycle times by eliminating intermediate steps in the conversion processes.

SUMMARY OF THE INVENTION

The present invention is accordingly directed to a method and apparatus for producing lower alkylene oxides and lower alkylene glycols by reacting at least one of a lower alkane and/or lower alkene with a source of oxygen and, optionally, a source of hydrogen to convert the lower alkane and/or lower alkene to at least one of the desired end products.

The necessary oxygen may be obtained from any suitable source, including without limitation, oxygen, ozone, and oxides of nitrogen. Preferably, oxygen is used to carry out the reaction. The $O_2$ may be fed at any concentration by mixing with $N_2$, He, or other inert gases. A convenient and safe source of oxygen is air. The required oxygen may also be provided by a suitable metal oxide catalyst or by the reaction of a metal oxide catalyst with $N_2O$, $NO_x$ or sulfur oxides which may be generated in situ or supplied to the reaction system indirectly. The term metal oxide as used herein includes oxides of single metals or multiple metals. In a preferred embodiment of the invention, the oxygen is supplied by one or more reducible metal oxide catalysts that are regenerated by exposure to air, $O_2$, other oxygen containing gases, or other suitable oxygen sources.

Additionally, a source of hydrogen may be directly or indirectly provided, for example, $H_2$ gas. The necessary hydrogen may also be provided by one or more hydrogenation/dehydrogenation metal catalysts.

In the preferred embodiment, the invention includes a metal or mixed metal oxide catalyst, which provides a favorable standard free energy for the selective partial oxidation reactions. Metal oxide catalysts have been found to be particularly suitable for synthesizing ethylene oxide or ethylene glycol by epoxidation and dihydroxylation, respectively. These types of metal oxides (referred to herein as "red-ox" catalysts) allow for the ready accessibility of lattice oxygen to promote the oxidation of the feed materials, which results in a corresponding reduction of the metal oxide. This is followed by re-oxidation of the catalyst by another oxygen source, such as $O_2$ or an oxygen-containing gas. Examples of effective red-ox catalysts include, but are not limited to, the oxides of cerium, iron, copper, nickel, lead, cadmium, molybdenum, vanadium, bismuth, manganese, barium, cobalt, strontium, tungsten, samarium, osmium, rhenium, rare earth elements, and mixtures of these oxides.

Those metals, which are generally known as hydrogenation/dehydrogenation metals, are also effective for carrying out the reaction, either alone or in combination with above-mentioned metal oxide catalysts. As explained in more detail below, it is believed that these catalysts generate highly reactive hydroperoxo and/or peroxo species from $O_2$ and $H_2$ and provide the oxygen and hydrogen necessary for the dihydroxylation or epoxidation reaction. These catalysts include but are not limited to nickel, palladium, platinum, cobalt, rhodium, iridium, iron, ruthenium, copper, zinc, gold, silver and mixtures of these metals.

Typically, both the red-ox and hydrogenation/dehydrogenation catalysts are supported on suitable carriers such as cerias, titanias, zirconias, silicas, aluminas, $\alpha$-alumina, silicon carbide, aluminum phosphate molecular sieves (AlPO's), high silica molecular sieve zeolites, MCM-type large pore zeolites, mixtures of these carriers, and other catalyst support materials well-known in the art.

Thus, in the preferred embodiment, the apparatus includes a lower alkane/alkene supply; an oxygen supply for providing a source of oxygen; and a metal oxide catalytic reactor. The metal oxide catalytic reactor includes a reactor chamber; and a phosphate modified catalyst in the chamber for reacting the lower alkane/alkene supply with the source of oxygen to convert the lower alkane/alkene by selective partial oxidation to at least one of the ethylene oxide and ethylene glycol.

Both the red-ox and hydrogenation/dehydrogenation catalysts can be modified with a phosphorus containing salt. While not wishing to be bound by theory, it is believed that this phosphate modification provides for isolation of metal sites which makes the both the red-ox and hydrogenation/dehydrogenation catalysts more active and selective for the dihydroxylation or epoxidation of ethane to produce ethylene glycol and ethylene oxide, respectively. The phosphate-modified catalyst may be prepared by adding a phosphorus containing salt (e.g., phosphoric acid, ammonium dihydrogen phosphate, sodium phosphate, etc.) using techniques familiar to one skilled in the art. Alternatively, the phosphate may be incorporated during the forming of the re-dox or hydrogenation/dehydrogenation by coprecipitation, sol gel method, or other methods known to one skilled in the art.

Also, in the preferred embodiment, the apparatus further includes a separator for separating the ethylene oxide and the ethylene glycol from the total product stream and from unconverted reactants. The separator includes an input line, a distillation device, and a product output line. The distillation device may be a flash evaporator or a distillation column, wherein the evaporation or distillation is carried out under conditions known in the art to obtain the desired product purity.

The apparatus may include a recycle line for returning unconverted reactants back to the reactor. In addition, the product output line may include at least two product output streams when intermediate products are desired.

In the preferred embodiment, the lower alkane/alkene supply is selected from the group consisting of butane/butylene; propane/propylene; and ethane/ethylene. Also, preferably, the lower alkane/alkene supply is substantially sulfur-free and phosphorous-free to reduce possible poisoning of the catalyst. The lower alkane/alkene supply is a two-carbon hydrocarbon, which is preferably ethane and/or ethylene.

The oxygen supply for providing a source of oxygen is at least one of oxygen, ozone and oxides of nitrogen. Preferably, the source of oxygen is $O_2$ or $N_2O$. In the preferred embodiment, the source of oxygen is provided by at least one metal oxide catalyst. The metal oxide catalyst includes at least one metal oxide that is reduced by reaction with a hydrocarbon moiety to a lower oxidation state such that the metal oxide provides a lower standard free energy for the selective partial oxidation of the lower alkane/alkene. The metal oxide may be selected from the group consisting of oxides of cerium, iron, copper, nickel, lead, cadmium, molybdenum, vanadium, bismuth, manganese, barium, cobalt, strontium, tungsten, samarium, osmium, rhenium, rare earth elements, and mixtures of these oxides. The metal oxide may be selected from the group consisting of NiO, PbO, CdO, $MoO_3$, $V_2O_4$, $V_2O_5$, BiO, $Bi_2O_3$, CuO, $Cu_2O$, $MnO_2$, $Mn_2O_3$, $Mn_3O_4$, $BaO_2$, $Co_3O_4$, $SrO_2$, $WO_2$, $WO_3$, $SnO_2$, $CeO_2$, $OsO_4$, $Re_2O_7$, FeO, $Fe_2O_3$, $Fe_3O_4$, rare earth oxides, and mixtures thereof.

The resulting alkylene oxides and alkylene glycols are substantially free of higher hydrocarbons greater than four carbon numbers.

According to the present invention, the metal oxide catalyst is regenerable. In the preferred embodiment, the metal oxide catalyst is regenerated by exposing the metal oxide catalyst to a source of oxygen, such as in a fixed bed, fluid bed, circulating fluidized bed, or other suitable reactor. Also, in the preferred embodiment, the apparatus may further include a hydrogen supply for providing a source of hydrogen in addition to the oxygen supply for providing a source of oxygen.

In the preferred embodiment, the phosphate-modified catalyst is iron phosphate. However, hydrogenation catalyst may work as well. The catalyst may further include a catalytic modifier, such as a platinum-containing compound, which improves the activity and/or selectivity of the catalyst. Other modifiers may also be used such as alkali and alkaline earth oxides. The apparatus may also include a carrier for supporting the phosphate-modified catalyst. In the preferred embodiment, the carrier is selected from the group consisting of: cerias, titanias, zirconias, silicas, aluminas, $\propto$-alumina, silicon carbide, aluminum phosphate molecular sieves (AlPO's), high silica molecular sieve zeolites, MCM-type large pore zeolites, mixtures thereof.

The present invention is operable to react the ethane/ethylene with oxygen to form the at least one of ethylene oxide and ethylene glycol and preferably forms ethylene glycol. However, the ethane/ethylene may also form higher glycols selected from the group consisting of diethylene glycol (DEG), triethylene glycol (TEG), and tetraethylene glycol (T4G).

As is expected the higher glycols are also formed as a result of condensation of the formed glycols and/or ethoxylation. In general, the lower glycol is preferred, but higher glycols may be formed preferentially by running at higher alkane/alkene conversions, or by recycle of the alkylene glycols back to the reactor.

Accordingly, one aspect of the present invention is to provide a method and apparatus for synthesizing at least one of alkylene oxides and alkylene glycols from lower alkanes and/or lower alkenes, the apparatus including: a lower alkane/alkene supply; an oxygen supply for providing a source of oxygen; and a metal oxide catalytic reactor for reacting the lower alkane/alkene supply with the source of oxygen to convert the lower alkane/alkene by selective partial oxidation to at least one of the alkylene oxides and alkylene glycols.

Another aspect of the present invention is to provide a metal oxide catalytic reactor for an apparatus for synthesizing at least one of alkylene oxides and alkylene glycols from lower alkanes and/or lower alkenes, the metal oxide catalytic reactor including: a reactor chamber; and a phosphate modified catalyst in the chamber for reacting the lower alkane/alkene supply with the source of oxygen to convert the lower alkane/alkene by selective partial oxidation to at least one of the alkylene oxides and alkylene glycols.

Still another aspect of the present invention is to provide a method and apparatus for synthesizing at least one of alkylene oxides and alkylene glycols from lower alkanes and/or lower alkenes, the apparatus including: a lower alkane/alkene supply; an oxygen supply for providing a source of oxygen; a metal oxide catalytic reactor, the metal oxide catalytic reactor including: a reactor chamber; and a phosphate modified catalyst in the chamber for reacting the lower alkane/alkene supply with the source of oxygen to convert the lower alkane/alkene by selective partial oxidation to at least one of the alkylene oxides and alkylene glycols; and a separator for separating the alkylene oxides and alkylene glycols from the total product stream and unconverted reactants.

These and other aspects of the present invention will become apparent to those skilled in the art after a reading of the following description of the preferred embodiment when considered with the drawings.

DESCRIPTION OF THE PREFERRED EMBODIMENTS

Figure 1:
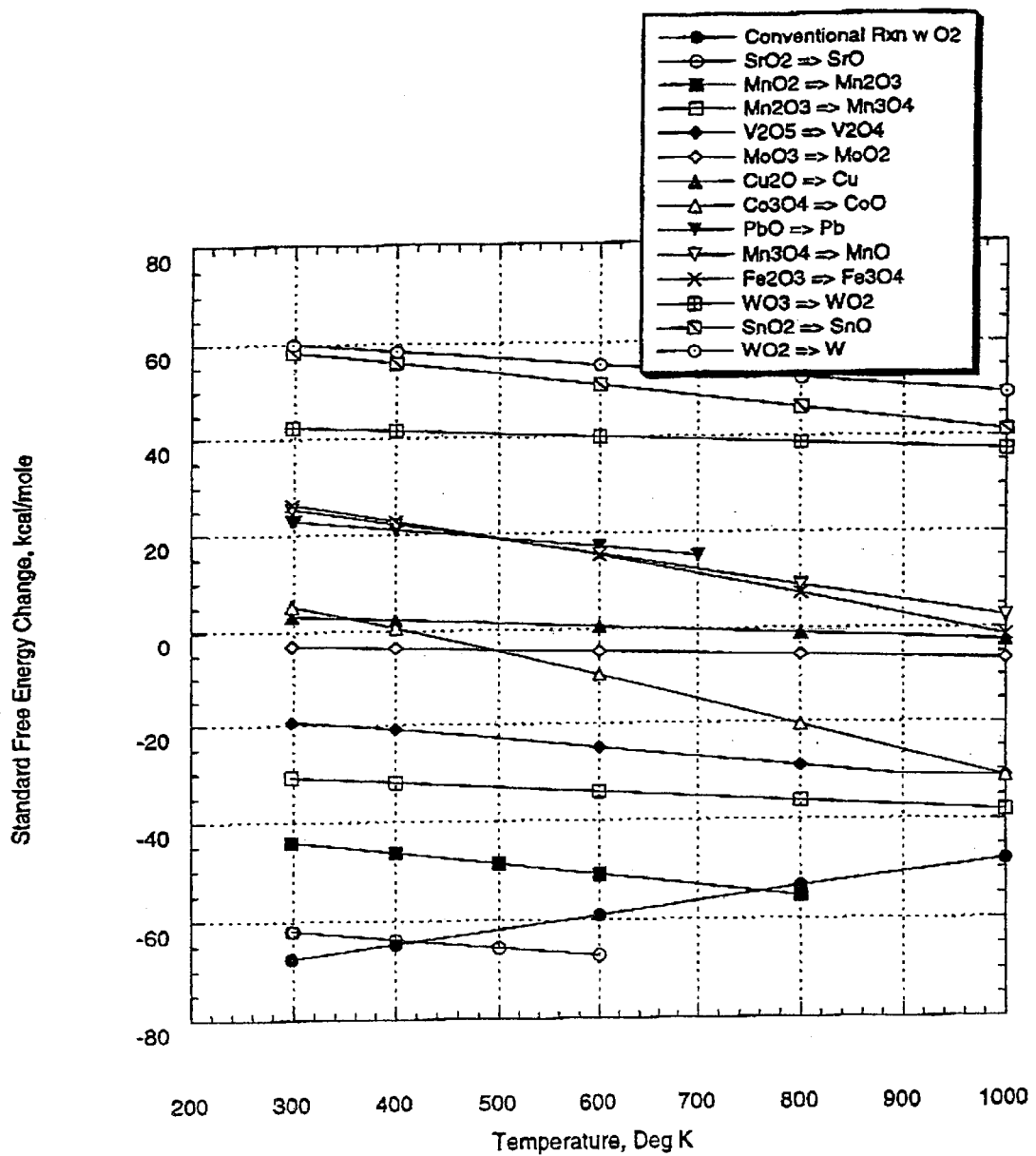
FIG. 1 contains a series of plots illustrating the standard free energy change as a function of temperature for a number of ethane based routes to monoethanolamine.

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms.

The present invention will be described in connection with an explanation of the synthesis of ethylene oxide or ethylene glycol from ethane. However, as will be apparent to those skilled in the art, the invention may be used to synthesize other alkylene oxides and alkylene glycols using other lower alkanes and/or lower alkenes as the hydrocarbon starting materials and other raw material feeds.

Four typical routes to ethylene glycol based on selective dihydroxylation of ethane, according to the present invention, are set forth below. In certain preferred embodiments using a regenerable metal oxide catalyst, a non-limiting example of which is provided in reaction (4) by Fe2O3, all four routes are actively being employed to provide ethylene glycol from ethane:

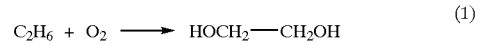
(1)

(2)

(3)

(4)

The reactions may be carried out in gas, liquid, supercritical, or multiphase media. As noted previously, any suitable source of oxygen may be utilized to convert ethane and/or ethylene to ethylene glycol. However, when the reactions are carried out in the vapor phase, $O_2$ gas or $N_2O$ are the most preferred forms of these reactants. As to the hydrocarbon raw materials, it should also be understood that the use of ethane and ethylene are not mutually exclusive, and that a mixture of these reactants may be utilized in the synthesis of ethylene glycol.

The reactions may be carried out over a broad range of temperatures and pressures. Generally, however, conditions of relatively low temperature and relatively high pressure are preferred. Lower temperatures tend to enhance selectivity and reduce or eliminate the formation of undesirable combustion by-products, such as CO, $CO_2$, etc. Higher pressures generally increase the rate at which the desired end products are formed. Typically, the synthesis is carried out at temperatures ranging from about 25° C. to about 500° C. and at pressures ranging from about 1 atmosphere to about 200 atmospheres.

While not intending to be limited to a particular theory or mechanistic pathway, the dihydroxylation, as represented in reactions (1)–(2), is believed to proceed by the formation of highly reactive hydroperoxo and/or peroxo species. Specifically, the metal oxide appears to react with either $O_2$ gas or $N_2O$ to form peroxo intermediates by oxidation of the metal oxide. These peroxo intermediates can be either peroxo or some reactive monatomic oxygen. While the oxygen is coming from the metal oxide, it may need a catalyst to relinquish this oxide.

In the most preferred embodiment of the invention, reactions (1)–(4) proceed over a reducible and regenerable metal oxide red-ox catalyst. Generally, metal oxides suitable for use in the invention are those metal oxides that are reduced by reaction with a hydrocarbon moiety to a lower oxidative state, such that the metal oxide provides a lower standard free energy for the selective partial oxidation reaction, in this particular case the reaction to produce ethylene glycol. Oxygen from the feed material then re-oxidizes the metal oxide. For the synthesis of ethylene glycol from ethane using a metal oxide as a source of oxygen, an exemplary reaction in which the metal oxide is re-oxidized by a source of oxygen (air) and then recycled back in a recycle reaction system, is shown as follows:

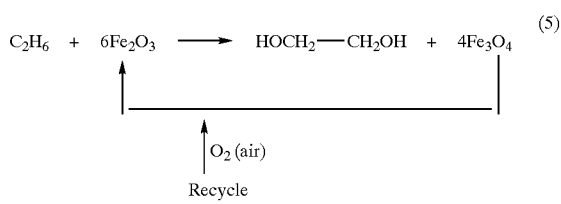
(5)

For other metal oxides, similar red-ox reactions can be depicted as shown above by balancing the appropriate valences and coefficients for the particular metal oxide selected.

It is believed that the necessary oxygen is provided by these catalysts as oxygen, which moves from the lattice to the surface (perhaps as $O^{-2}$, $O^-$, or $O_2^-$ surface species). One possibility that may account for the high activity of these catalysts is that the metal oxides have point defects, step defects, other types of defects or disorders, or cation vacancies within the lattice, which provides for the ready accessibility of oxygen.

Whatever the basis for their highly active nature, a number of metal oxides are particularly suitable for carrying out the selective partial oxidation of alkanes and alkenes including NiO, PbO, CdO, $MoO_3$, $V_2O_4$, $V_2O_5$, BiO, $Bi_2O_3$, CuO, $Cu_2O$, $MnO_2$, $Mn_2O_3$, $Mn_3O_4$ $BaO2$, $Co_3O_4$, $SrO_2$, $WO2$, $WO_3$, $SnO_2$, $CeO_2$, $OsO_4$, $Re_2O_7$, FeO, $Fe_2O_3$, $Fe_3O_4$, rare earth oxides, and mixtures of these metal oxides.

While not intending to be limited to a particular theory or mechanistic pathway, the dihydroxylation, as represented in reaction (3), also is believed to proceed by the formation of highly reactive hydroperoxo and/or peroxo species. Specifically, the metal oxide appears to react with $H_2$ gas to form a hydroperoxo intermediate species with a further elimination of $H_2O$ to produce the peroxo species.

These intermediates are also formed by reaction of a hydrogenation/dehydrogenation metal catalyst with $O_2$ and then by reaction with $H_2$. The oxygen adsorbed on the catalyst, either as the hydroperoxo or peroxo intermediate, is capable of adding to an olefin which has been added either as a feed material, or generated in situ by oxidation of an alkane. The intermediate generated from reaction of the oxygen with the olefin is an epoxide. The epoxide may then react with water to give the glycol.

For example, a feed of ethylene and/or ethane with $H_2$ and $O_2$ would produce ethylene oxide as an intermediate which would react with $H_2O$ to produce ethylene glycol. Typically, reaction conditions such as $O_2/H_2$ mole ratios, pressure, and temperature are controlled to give the desired end product. Those hydrogenation/dehydrogenation metals that are the most active include, but are not limited to, nickel, palladium, platinum, cobalt, rhodium, iridium, iron, ruthenium, copper, zinc, gold, and silver and mixtures of these metals.

The red-ox and hydrogenation/dehydrogenation catalysts described herein can be prepared by conventional procedures known in the art. For example, the catalyst can be incorporated on preformed carriers or supports (these terms are used interchangeably herein) by impregnating the carrier with a liquid solution comprising a form of the element required to effect reaction. The support shape is generally not narrowly critical; accordingly, the carrier may take the form of, for example, pellets, extruded particles, spheres, rings, monoliths and the like.

If more than one metal is to be incorporated the metals may be incorporated simultaneously or sequentially, the sequence of which is not narrowly critical. As noted above, typical supports include cerias, titanias, zirconias, silicas, aluminas, α-alumina, silicon carbide, aluminum phosphate molecular sieves (AlPO's), high silica molecular sieve zeolites, MCM-type large pore zeolites, mixtures of these carriers, and other catalyst support materials well known in the art.

Generally, the metal is in the form of a salt which can be easily dissolved in a liquid solvent for incorporation into the particles or monolith structure of the carrier. Several impregnation steps may be required depending on the amount of metal or metal oxide required and the solubility of the salt of the catalytic compound in the solvent. A drying step is generally employed between each impregnation. This is a well-known procedure in the art for incorporating metals and metal oxides onto a solid support material. After all of the impregnation steps are completed, the material is then usually heated at higher temperatures, typically from 100–900° C., to effect at least partial decomposition of the salt to the metal oxide.

Alternatively, the metal salt may be heated to 100–900° C. after each impregnation and drying step. The drying and heating steps may be done incrementally at various temperatures over suitable periods of time, or these steps can be ramped up to the desired temperature fairly linearly. If desired, the metal oxide can be reduced to the metal, at least partially, with hydrogen or other reducing gases (e.g. carbon monoxide) using methods well known to one skilled in the art.

Alternatively, some form of the requisite metal can be fused, bonded or compressed into solid pellets or larger structures, or composited with one or more support materials, in association with one or more metal oxides and heated as above. The material may be reduced as alluded to above.

Still further, the catalyst can be provided at the time of preparing the support material. For example, one or more metal oxides may be condensed from their respective hydrolyzable monomers to the desired oxides to form oxide powders which can thereafter be blended and compressed to form pellets and larger structures of the catalyst. The materials are then heated and optionally reduced as alluded to above.

In yet another approach, the metal salt may be precipitated on a preformed carrier using methods described in the art. This procedure offers some advantages for depositing the active metal on the outside of the carrier which may lead to improved selectivity. Some further advantages may be realized by preparing the selective partial oxidative amination catalyst on zeolite-type materials. For zeolites, known ion-exchange procedures may be employed to incorporate various catalytic metal ions. This allows for shape selectivity and can enhance selective partial oxidation over complete oxidation. The procedures for incorporating metals on zeolites are well known.

The use of supports for the catalysts provides a number of significant advantages. Some of the catalysts are not structurally stable under the reaction conditions when utilized over an extended period of time. In a batch reaction, this is not a significant issue. However, when the reaction is effected with the catalyst as part of a fixed bed reactor, in a tubular reactor, or in a fluid bed reactor it is desirable that the catalyst have greater structural stability/integrity for the reaction medium.

Attrition can be a significant problem with an unsupported catalyst particularly if used in a fluidized bed reactor. Improved resistance to attrition of the catalyst can be achieved by providing an attrition resistant coating on the surface of the catalyst. The coating should be resistant to the reactants and products and must be sufficiently porous to permit free passage of the reactants and products through the coating to the catalyst site. Polysilicic acid, zinc oxide, titanium oxide, zirconium oxide, other metal oxides and mixtures of these oxides may be used to provide an outer coating on the catalyst which provides better attrition resistance. The techniques used to provide a protective coating are well known to one skilled in the art.

In one embodiment of the invention, the reducible metal oxide catalyst has a microstructure characterized by a plurality of porous microspheres. An attrition resistant coating is provided on the surface of the microspheres. In this particular example, the coating comprises polysilicic acid. However, as mentioned above the coating may be formed from other inert materials that will also provide attrition resistance, such as zinc oxide, $TiO_2$, $ZrO_2$, and other metal oxides.

Referring now to the synthesis of ethylene oxide, the conversion of ethane to form ethylene oxide is represented by the following reactions:

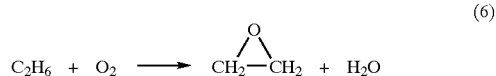
(6)

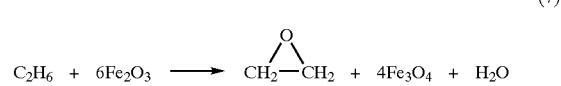
(7)

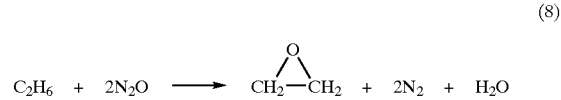
(8)

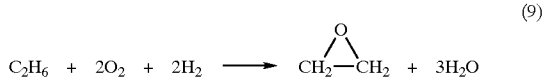

(9)

As discussed above, with respect to reaction (3), it is expected that the metal oxide will react with $H_2$ gas to form a hydroperoxo intermediate species with a further elimination of $H_2O$ to produce the peroxo species. Also, the epoxidation of ethane to ethylene oxide proceeds under essentially the same reaction conditions and in essentially the same manner as that described above in connection with the synthesis of ethylene glycol. Accordingly, the reactions may be carried out in gas, liquid, supercritical or multiphase media.

Various sources of oxygen and hydrogen may be utilized to convert ethane to ethylene oxide; however, oxygen gas, preferably mixed with an inert gas, and hydrogen is preferred. Either ethane or ethylene may be used as the starting hydrocarbon raw material for the synthesis of ethylene oxide, or, a mixture of these starting materials may be employed. The epoxidation reactions may be carried out over a broad range of temperatures and pressures. In general, similar conditions discussed above for the synthesis of ethylene glycol are used for the synthesis of ethylene oxide with one notable exception. The reactants are generally diluted with an inert gas (e.g., nitrogen or helium) to minimize the reaction between the coproducts ethylene oxide and water to form ethylene glycol. However, the same conditions of relatively low temperature and relatively high pressure discussed above in connection with the synthesis of ethylene glycol are preferred. Thus, the synthesis of ethylene oxide is typically carried out at temperatures ranging from about 25° C. to about 500° C. and at pressures ranging from about 1 atmosphere to about 200 atmospheres.

As in the case of ethylene glycol, the epoxidation of ethane and/or ethylene to produce ethylene oxide is preferably carried out over a reducible metal oxide catalyst, which provides the oxygen necessary for the reaction. The metal oxides suitable for synthesizing ethylene oxide are expected to be the same catalysts described above in connection with the synthesis of ethylene glycol.

In a preferred embodiment of the invention, the catalyst is continuously regenerated and recycled as illustrated in reactions (10) and (11):

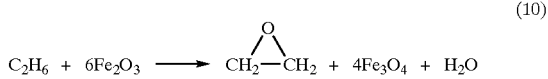

(10)

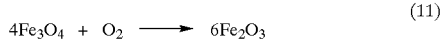

(11)

For other metal oxides, similar red-ox reactions can be depicted as shown above by balancing the appropriate valences and coefficients for the particular metal oxide selected.

Figure 2:
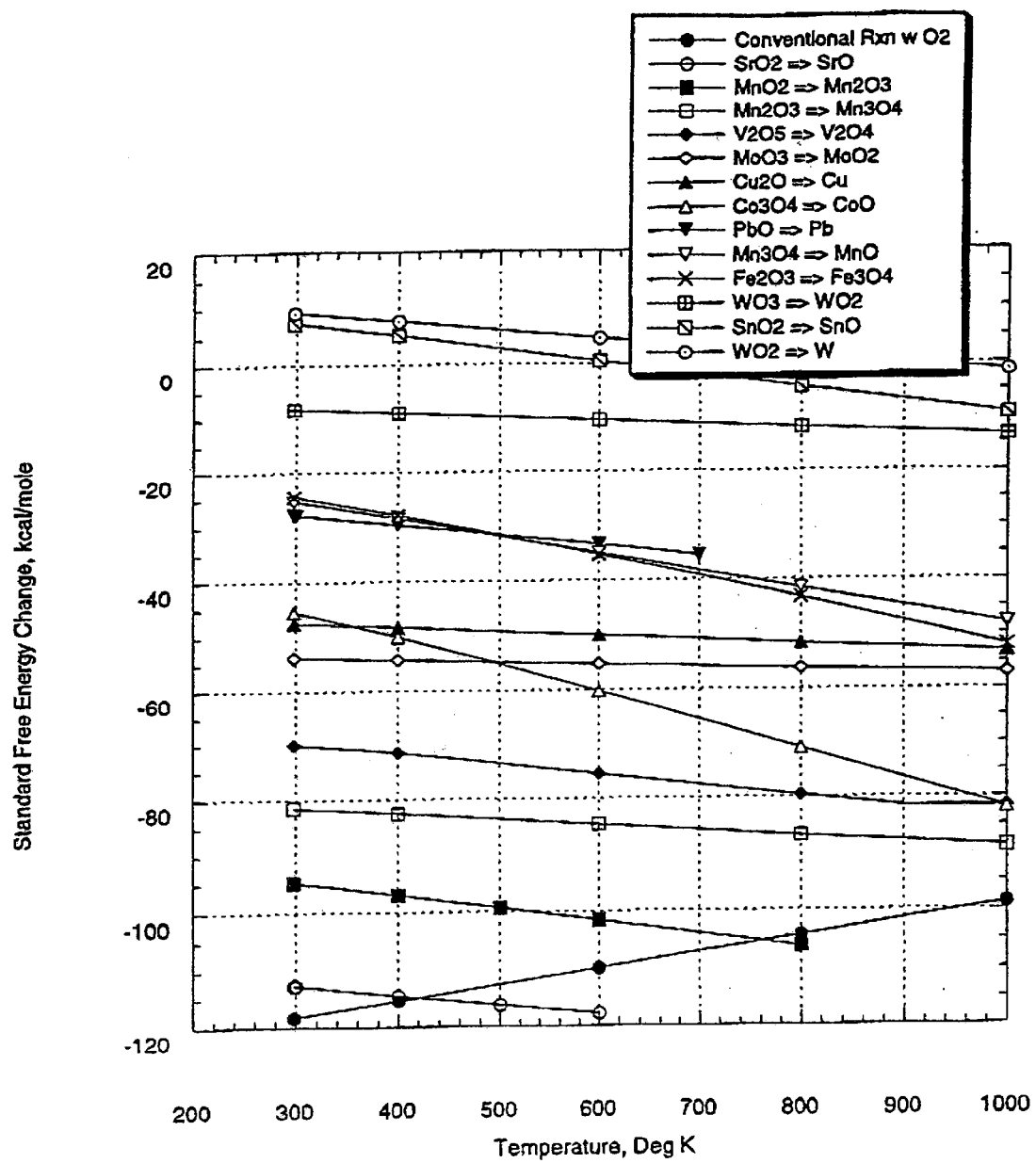
FIG. 2 contains a series of plots illustrating the standard free energy change as a function of temperature for a number of ethane based routes to ethylenediamine.
Figure 3:
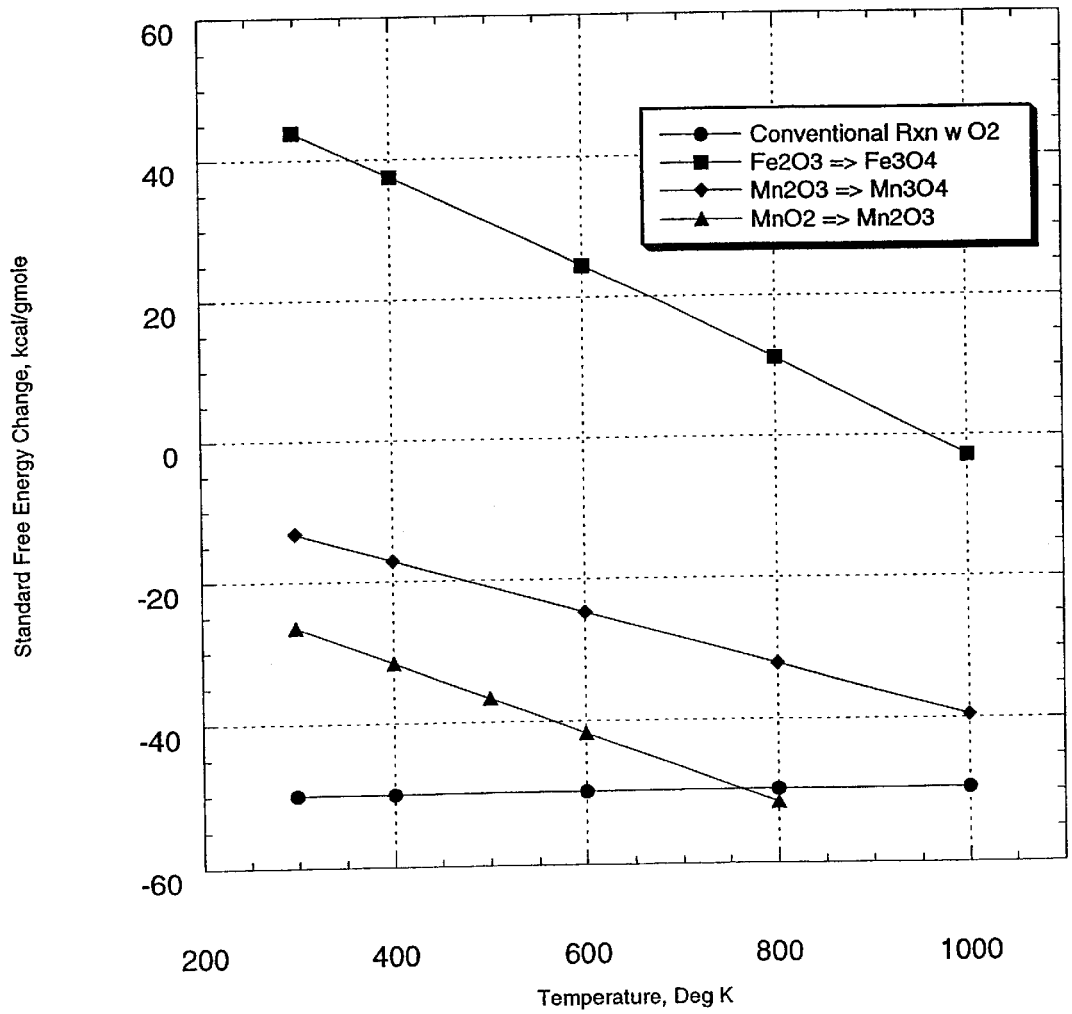
FIG. 3 contains a series of plots illustrating the standard free energy change as a function of temperature for a number of ethane based routes to ethylene oxide.
Figure 4:
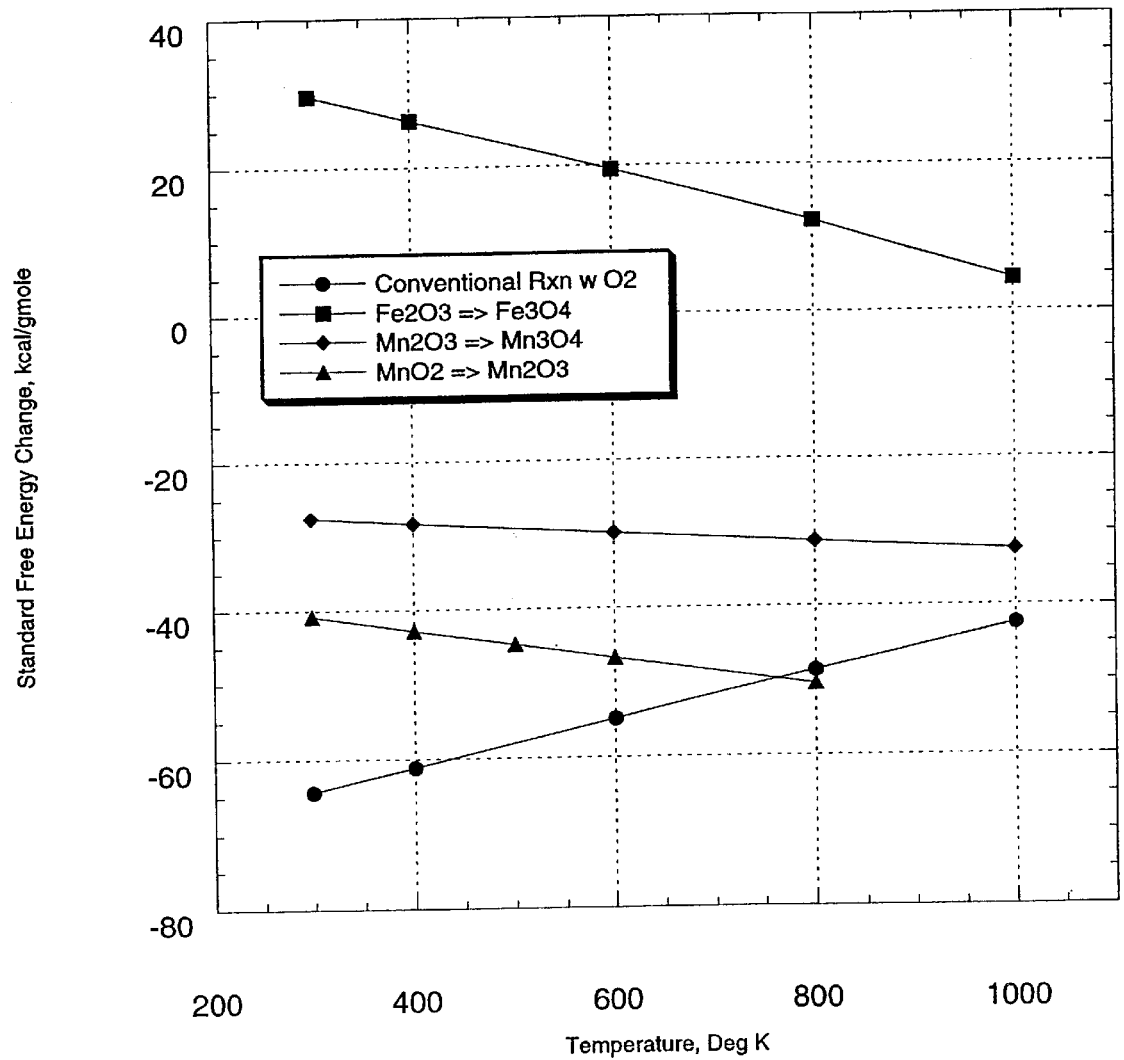
FIG. 4 contains a series of plots illustrating the standard free energy change as a function of temperature for a number of ethane based routes to ethylene glycol.

Turning now to the Figures, FIGS. 1 and 2 correspond to FIGS. 3 and 4 in U.S. patent application Ser. No. 09/430,634, filed Oct. 29, 1999, now U.S. Pat. No. 6,281,387, entitled "Process and Catalyst for Synthesizing Aliphatic, Cyclic and Aromatic Alkanolamines and Alkyleneamines", the entire disclosure of which is hereby incorporated by reference. FIG. 1 contains a series of plots illustrating the standard free energy change as a function of temperature for a number of ethane based routes to monoethanolamine. FIG. 2 contains a series of plots illustrating the standard free energy change as a function of temperature for a number of ethane based routes to ethylenediamine. These Figures illustrated that there were no thermodynamic barriers to the conversion of ethane to either monoethanolamine or ethylenediamine.

Similarly, FIGS. 3 and 4 illustrate that there are no thermodynamic barriers to the conversion of ethane to ethylene oxide and ethylene glycol by epoxidation and dihydroxylation, respectively. The non-catalyzed reaction which utilizes oxygen gas as the source of the required oxygen exhibits a highly favorable standard free energy change in all cases. Somewhat less favorable, but still thermodynamically advantageous free energy changes are provided by the use of a suitable metal oxide catalyst or a hydrogenation/dehydrogenation metal catalyst.

The chief advantages provided by the use of these catalysts are enhanced selectivity and increased conversion of the hydrocarbon starting materials to ethylene glycol and ethylene oxide. At the same time, the generally lower reaction temperatures at which highly active catalysts operate tend to minimize or eliminate the formation of combustion products. For example, FIGS. 3 and 4 illustrate that a reducible $MnO_2$ catalyst provides a very favorable standard free energy change at a temperature of about 250° K. (−23.6° C.) for the dihydroxylation of ethane and epoxidation of ethane to ethylene glycol and ethylene oxide, respectively.

The reaction may be effected by the incremental addition of one of the reactants to the other or by the joint addition of the reactants to the catalyst. The reaction may be carried out by slurrying the catalyst in the reactants (optionally in a solvent) or in a batch or semi-batch mode in an autoclave. Solvents may be used to provide two liquid phases one of which contains the selective partial oxidation catalyst and the other the reactants with a sufficient amount of mixing to effect reaction. A more preferred method effects the reaction in a continuous manner in a fixed bed or fluidized bed over the selective partial oxidation catalyst.

Inorganic membrane reactors may be used to control the concentration of reactants (e.g., oxygen) in the metal oxide catalyst bed, and/or to provide a source of the metal oxide catalyst. The reactor may be an inert membrane packed bed reactor (IMPBR), an inert membrane fluidized bed reactor (IMFBR), a catalytic membrane reactor (CMR), a packed bed catalytic membrane reactor (PBCMR), or a fluidized bed catalytic membrane reactor (FBCMR).

Figure 5:
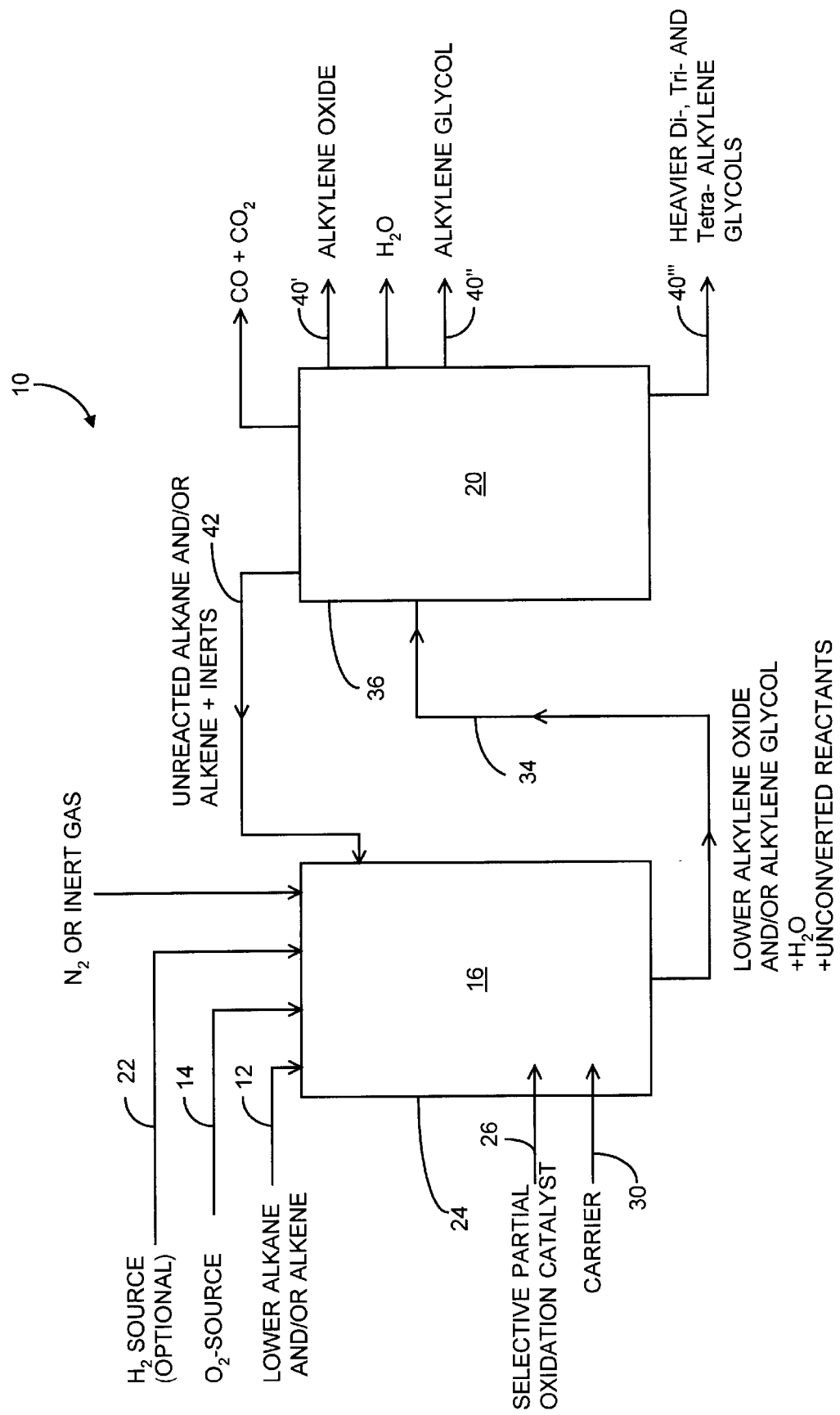
FIG. 5 is a block diagram illustrating an apparatus for converting ethane to ethylene oxide and ethylene glycol constructed according to the present invention.

In a preferred embodiment shown schematically in FIG. 5, the reaction is carried out in an apparatus 10 which includes a lower alkane/alkene supply 12, an oxygen supply 14, and a metal oxide catalytic reactor 16. The apparatus 10 may further include a separator 20 for separation of multiple reaction products. The lower alkane/alkene supply 12 may supply ethane/ethylene, butane/butylene, and/or propane/propylene.

Preferably, the lower alkane/alkene supply 12 is substantially free of sulfur and phosphorous. The oxygen supply 14 may be oxygen, oxides of nitrogen, or ozone, and may additionally include a source of hydrogen 22.

The metal oxide catalytic reactor 16 includes a chamber 24 and a modified phosphate catalyst 26 in the chamber 24, which is preferably iron phosphate. The catalyst may include a modifier, preferably containing platinum. A carrier 30 may also be provided for supporting the catalyst 26 in the reactor 16. The carrier 30 may be selected from the group consisting of cerias, titanias, zirconias, silicas, aluminas, α-alumina, silicon carbide, aluminum phosphate molecular sieves (AlPO's), high silica molecular sieve zeolites, MCM-type large pore zeolites, and mixtures thereof.

The separator 20 includes an inlet 34, a distillation device 36, and a product output 40. Alternatively, the separator may have at least two output streams 40' and 40". The separator 20 may also include a recycle line 42 for transferring unconverted reactants back to the reactor 16. The distillation device 36 may be a flash evaporator that utilizes vapor pressure differentials to separate multiple products. Alternatively, the distillation device 36 may be a distillation column, which uses product temperature differentials for separation.

The use of a circulating fluidized bed reactor provides a number of advantages. The essentially plug flow characteristics of gas and catalyst particles in the riser give high selectivity to ethylene oxide and ethylene glycol, and the absence of oxygen gas in the riser further improves selectivity by reducing destruction of the ethylene oxide and ethylene glycol as well as the ethane/ethylene. Specifically, the essentially plug flow characteristics of gas and catalyst particles in the riser give high selectivity to ethylene oxide and ethylene glycol by minimizing backmixing, and the absence of oxygen gas in the riser further improves selectivity by reducing combustion of the ethylene oxide and ethylene glycol to $CO_x$ and water.

Loosely bound highly active oxygen species are eliminated prior to entry into the riser, which results in increased conversion and the maintenance of high catalyst selectivity. The high circulation rate of the catalyst also provides a heat sink which helps control the temperature in the riser and reduces the heat transfer area that would otherwise be required to remove the heat of reaction. Accordingly, the reactor design provides economic as well as process advantages.

While the use of a circulating fluid bed reactor provides important advantages, it should be understood that the invention is not limited in this regard. It should also be understood that regardless of which type of reactor is utilized, should the metal oxide catalyst not provide sufficient oxygen small amounts of additional $O_2$ may be bleed into the reaction system. Typically, if additional oxygen is required it is added in an amount less than about 5%, and preferably less than about 2%, based on the total feed.

As noted previously, the present invention has been described in detail in the context of producing ethylene glycol and ethylene oxide by the dihydroxylation or epoxidation of ethane. However, those skilled in the art will readily appreciate that the invention has general application for the production of other alkylene oxides and alkylene glycols from a variety of alkane and alkene starting materials. For example, propane/propylene to 1,2 propanediol; 1,3 propanediol; and propylene oxide. Also, butane to 1,2 butanediol; 1,3 butanediol; 1,4 butanediol; 2,3 butanediol; 2,4 butanediol; and butylene oxides.

Those skilled in the art also will readily appreciate that the reactions described above are not mutually exclusive. That is, either ethylene glycol or ethylene oxide may be produced, or both of these products may be produced simultaneously. The particular product(s) produced and the particular route (s) by which this is accomplished are determined by controlling the partial pressure of the raw materials, the temperature of the reactor and the choice of a suitable catalyst. Accordingly, the present invention provides a practicable and economic means of producing a wide variety of alkylene oxides and alkylene glycols based on the use of alkanes and/or alkenes as the hydrocarbon starting materials.

Certain modifications and improvements will occur to those skilled in the art upon a reading of the foregoing description. It should be understood that all such modifications and improvements have been deleted herein for the sake of conciseness and readability but are properly within the scope of the following claims.

We claim:

1. A method for synthesizing at least one of alkylene oxides and alkylene glycols from lower alkanes and/or lower alkenes, said method comprising the steps of:
   (a) providing a source of lower alkane/alkene;
   (b) providing a source of oxygen; and
   (c) reacting said source of lower alkane/alkene with said source of oxygen to convert said lower alkane/alkene by selective partial oxidation in the presence of a catalyst to at least one of said alkylene oxides and alkylene glycols.

2. The method according to claim 1, wherein said catalyst is a metal oxide or mixed metal oxide catalyst.

3. The method according to claim 1, wherein said catalyst includes both metal oxide and mixed metal oxide catalysts.

4. The method according to claim 1, wherein said catalyst is phosphate-modified.

5. The method according to claim 1, wherein said catalyst further includes a catalytic modifier including a platinum containing compound.

6. A method for synthesizing at least one of alkylene oxides and alkylene glycols from lower alkanes and/or lower alkenes, said method comprising the steps of:
   (a) providing a source of lower alkane/alkene;
   (b) providing a source of oxygen; and
   (c) reacting said source of lower alkane/alkene with said source of oxygen in the presence of a phosphate modified catalyst to convert said lower alkane/alkene by selective partial oxidation to at least one of said alkylene oxides and alkylene glycols.

7. A method for synthesizing at least one of alkylene oxides and alkylene glycols from lower alkanes and/or lower alkenes, said method comprising the steps of:
   (a) providing a source of lower alkane/alkene;
   (b) providing a source of oxygen; and
   (c) reacting said source of lower alkane/alkene with said source of oxygen in the presence of a phosphate modified catalyst to convert said lower alkane/alkene by selective partial oxidation to at least one of said alkylene oxides and alkylene glycols; and
   (d) separating said alkylene oxides and said alkylene glycols from the total product stream and the unconverted reactants.

8. The method according to claim 1, wherein said lower alkane/alkene supply is ethane/ethylene.

9. The method according to claim 1, wherein said oxygen supply for providing a source of oxygen is at least one of oxygen, ozone and oxides of nitrogen.

10. The method according to claim 2, wherein said the metal oxide is selected from the group consisting of oxides of cerium, iron, copper, nickel, lead, cadmium, molybdenum, vanadium, bismuth, manganese, barium, cobalt, strontium, tungsten, samarium, osmium, rhenium, rare earth elements, and mixtures of these oxides.

11. The Method according to claim 10, wherein said metal oxide is selected from the group consisting of NiO, PbO, CdO, $MoO_3$, $V_2O_4$, $V_2O_5$, BiO, $Bi_2O_3$, CuO, $Cu_2O$, $MnO_2$, $Mn_2O_3$, $Mn_3O_4$ $BaO2$, $Co_3O_4$, $SrO_2$, WO2, $WO_3$, $SnO_2$, $CeO_2$, $OsO_4$, $Re_2O_7$, FeO $Fe_2O_3$, $Fe_3O_4$, rare earth oxides, and mixtures thereof.

12. The method according to claim 2, wherein said metal oxide or mixed metal oxide catalyst is regenerable.

13. the method according to claim 1, wherein said lower alkane/alkene is reacted with oxygen to form said at least one of ethylene oxide and ethylene glycol.

14. The method according to claim 1, wherein said lower alkane/alkene forms higher glycols selected from the group consisting of diethylene glycol (DEG), triethylene glycol (TEG), and tetraethylene glycol (T4G).

15. The method according to claim 4, wherein said phosphate is iron phosphate.

* * * * *